(12) United States Patent
Wils

(10) Patent No.: US 6,203,324 B1
(45) Date of Patent: Mar. 20, 2001

(54) SET OF DENTAL IMPLANTS AND DENTAL IMPLANT USED THEREFOR

(76) Inventor: Ronald Peter Joannes Wils, Esschestraat 79, NL-5262 BB Vught (NL)

(*) Notice: Subject to any disclaimer, the term of this patent is extended or adjusted under 35 U.S.C. 154(b) by 0 days.

(21) Appl. No.: 09/428,231

(22) Filed: Oct. 27, 1999

(30) Foreign Application Priority Data

Oct. 27, 1998 (NL) .................................................. 1010409

(51) Int. Cl.$^7$ ...................................................... A61C 8/00
(52) U.S. Cl. ............................................ 433/173; 433/221
(58) Field of Search ...................................... 433/172, 173, 433/174, 175, 201.1, 220, 221, 224, 225

(56) References Cited

U.S. PATENT DOCUMENTS

| | | |
|---|---|---|
| 5,199,873 | 4/1993 | Schulte et al. . |
| 5,527,182 | 6/1996 | Willoughby . |
| 5,762,499 * | 6/1998 | Dard et al. ............................ 433/173 |
| 5,788,497 * | 8/1998 | Chalifoux ......................... 433/221 X |

FOREIGN PATENT DOCUMENTS

| | | |
|---|---|---|
| 90 02 823 | 6/1990 | (DE) . |
| 0 819 410 | 1/1998 | (EP) . |
| WO 98/52490 | 11/1998 | (WO) . |

* cited by examiner

*Primary Examiner*—Nicholas D. Lucchesi
(74) *Attorney, Agent, or Firm*—Young & Thompson

(57) ABSTRACT

A series of dental implants is proposed, each of which is stepped, the drill diameter for the largest step section of the smaller implant corresponding to the drill diameter for the smaller stepped section of the subsequent larger implant. The invention also relates to a dental implant consisting of a stepped shaft section provided close to the superstructure end with an external engagement surface for fitting the superstructure thereover. A collar, joined to the shaft section, extends around the external engagement surface at some distance therefrom. The internal surface thereof is conically divergent with respect to the axis of the shaft section and part of the superstructure can be placed in a stable manner in the space delimited between the inner surface of the collar and the external engagement surface.

9 Claims, 4 Drawing Sheets

SET OF DENTAL IMPLANTS AND DENTAL IMPLANT USED THEREFOR

FIELD OF THE INVENTION

The present invention relates to a set of dental implants and an implant.

BACKGROUND OF THE INVENTION.

U.S. Pat. No. 5,199,873 discloses a dental implant consisting of a number of successive threaded sections of different diameter. Compared with a long continuous threaded section, such a construction has the advantage that the insertion distance covered by screwing can be appreciably shortened for equally good anchoring. As a result the load on the bone material can be limited and the insertion time can be shortened. In practice implants of this type with different dimensions are used. Drills must be used to produce the relevant openings in the jawbone. If the screw thread is conical, it is customary for a cylindrical drill to be used, a firm join to the jaw being obtained as a result of the conical nature of such a screw thread.

SUMMARY OF THE INVENTION

The aim of the present invention is as far as possible to restrict the number of drills that have to be used in a set of implants.

This aim is achieved with a set as described above in that a series of at least two implants of different diameter, each implant being stepped, with a smaller and a larger section is provided wherein the drill diameter for the smaller section of an implant corresponds to the drill diameter for the larger section of a subsequent smaller implant.

The system of dental implants described above is advantageously used with implants comprising a shaft section provided, close to the end to be provided with a superstructure, with an external engagement surface for an instrument, for screwing in the implant, and for receiving said superstructure, the external engagement surface being at least partially surrounded by a peripheral collar located some distance therefrom and extending from the shaft. By this means an external engagement surface for an instrument for screwing in the implant is obtained with which the stability of the superstructure subsequently to be fitted is improved. Such an instrument can be a (ring or box) spanner. In this context it is possible that the collar extends less far than the external engagement surface (always with reference to the free end of both components), extends equally as far as or extends further than the related engagement surface.

It is also possible by means of construction of both the collar and the external engagement surface to give the annular space that is delimited between them any shape, which makes possible, on the one hand, optimal engagement of the engagement surface by the related instrument and, on the other hand, optimal fixing of the superstructure. In the case of an advantageous embodiment of the invention, the internal surface of the collar is, to this end, made such that it diverges conically towards the free end thereof. By this means a centring, clamping effect of the superstructure is provided if the latter is provided with a corresponding or somewhat deviating cone. The engagement end can have any shape known from the prior art. It can be of cylindrical construction, for example, hexagonal or octagonal construction. It is also possible to construct the engagement end such that it conically tapers somewhat towards the free end. In this case as well, the shape can be hexagonal, octagonal or polygonal in some other way.

Surprisingly it has been found that much more stable fixing of the superstructure can be obtained with only a slight rise in the cost price for the production of the implant. Moreover, it is possible to provide the external surface of the collar with any desired shape. This surface can likewise be of conically divergent construction, but of cylindrical construction in other embodiments.

Using the construction described above it is possible to position the free end of the engagement surface considerably lower than in the prior art. As a result, the cover screw which is placed over the engagement surface after implantation is located much lower. Moreover, this means that the tilting moment exerted on the implant during chewing is much lower. The lower location offers many more prosthetic possibilities, especially in the case of a complex external superstructure.

If use is made of a collar which is of conically divergent construction, the angle of said cone with respect to the longitudinal axis of the implant is preferably in the range between 40 and 50° and more particularly is approximately 45°. By selecting said angle in this way, optimum adjustment of the superstructure or the secondary component is possible.

If the collar also extends conically on the outside, a smooth transition to the superstructure or the secondary component is possible.

That part of the implant that extends into the jaw can be provided with transverse openings and/or other means promoting adhesion with the jawbone.

It must be understood that the set of dental implants described above can also be used on dental implants other than those described above, that is to say implants with which the engagement surface for an instrument is internal or with which a collar such as that described above is not present.

According to a further aspect the series of implants as described above is used in dental implants comprising from the insertion end a tapering first thread section, an adjoining cylindrical section, a further tapering thread section of which the core diameter at least corresponds to the core diameter of the first thread and an adjoining free end section, wherein the implant internally comprises a threaded section having adjoining means preventing rotation of a later super structure as well as a conical end section, said conical end section being embodied to have a tool engaged thereto.

The invention relates both to single stage and to two-stage implants. Moreover, it is possible for some parts of the implant optionally to be provided with a screw thread.

SHORT DESCRIPTION OF THE DRAWINGS

The invention will be explained in more detail below with reference to illustrative embodiments shown in the drawing. In the drawing.

DESCRIPTION OF THE PREFERRED EMBODIMENTS

Figure 1:
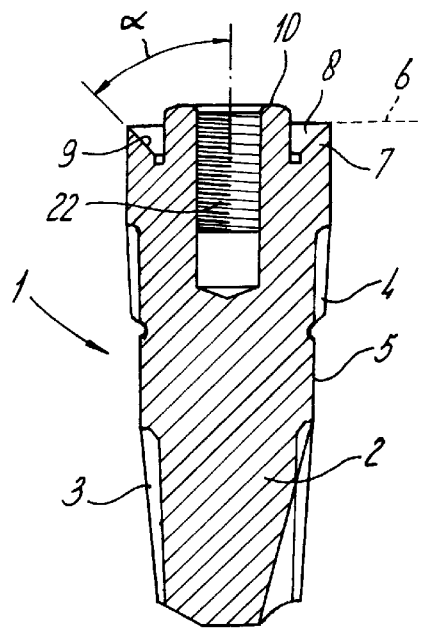
FIG. 1 shows, in cross-section, a first embodiment of a dental implant according to the invention.

In FIG. 1 (a two-stage implant) a first embodiment of a dental implant is indicated in its entirety by 1. This implant consists of a shaft section 2 provided with a conical threaded section 3 close to the insertion end. The conical screw thread is self-tapping, whilst the conical shape of the core diameter of the screw thread deviates from the conical shape of the external diameter, that is to say the screw thread does not have to be tapped. Close to the end where the superstructure, which is not shown, has to be fitted there is a somewhat conical threaded section 4, the pitch of which is constant. A smooth cylindrical section 5 is constructed between section 4 and section 3. The length thereof is dependent on a number of factors, such as the thickness of the patient's jawbone, and various lengths are available to the dentist. Threaded section 4 can be self-tapping if it is of somewhat conical construction. However, for harder bone it is advisable to tap screw thread into the bone beforehand.

6 indicates the line to which the implant is inserted in the jaw, that is to say the transition from the gingiva to the bone. It can be seen from FIG. 1 (a two-stage implant) that this upper limit corresponds to the extremity of a collar 7 that is arranged around hexagon 10. Hexagon 10 protrudes somewhat above collar 7. The space between collar 7 and hexagon 10 is indicated by 8. It can be seen from FIG. 1 that the internal surface of collar 7 is of conical construction and this is indicated by 9. The interior of hexagon 10 is provided with a screw thread 22 for securing a superstructure or secondary component. Such a superstructure or secondary component, which is not shown, is, on the one hand, placed over hexagon 10 but, on the other hand, engages on the external surface of the conical section 9. As a result optimum stabilisation takes place and transverse forces exerted on the secondary component or the superstructure can easily be taken up by the implant without high tilting moments being produced.

Figure 2:
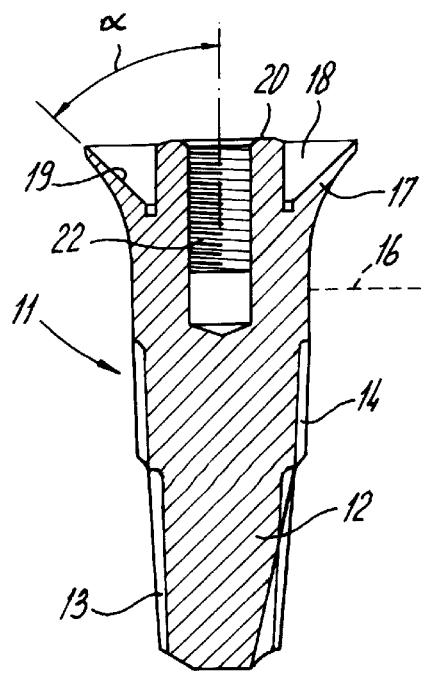
FIG. 2 shows, in cross-section corresponding to FIG. 1, a second embodiment of a dental implant according to the invention.

A variant of the construction according to FIG. 1 is shown in FIG. 2 (a single stage implant). This variant is indicated in its entirety by 11. The implant 11 is provided with a shaft section 12 and, like the above embodiment, with a lower threaded section 13 and an upper threaded section 14, which, however, in the case of this embodiment directly adjoin one another. The bone-gingiva transition line is indicated by 16 and is located substantially lower, that is to say the implant protrudes appreciably further (for example 3 mm) from the bone material. A member construction can be placed directly on top of this, without the intervention of a secondary component as in the case of a two-stage implant. The same secondary components can be used with both single stage and two-stage implants. Here the collar according to the invention is indicated by 17 and delimits a space 18 between the engagement surface now constructed as hexagon 20. The outside of collar 17 is likewise of conical construction, so that the superstructure will adjoin this with a fluid transition. Once again, a screw thread 22 has been made in the interior of hexagon 20. The cone angle between the axis 15 and the conical section 19 is indicated by α. According to the invention, this angle is preferably in the range between 40 and 50° and more particularly said angle is approximately 45°. It can be seen from FIG. 2 that the hexagon hardly protrudes beyond the free end of the collar 17.

Figure 5:
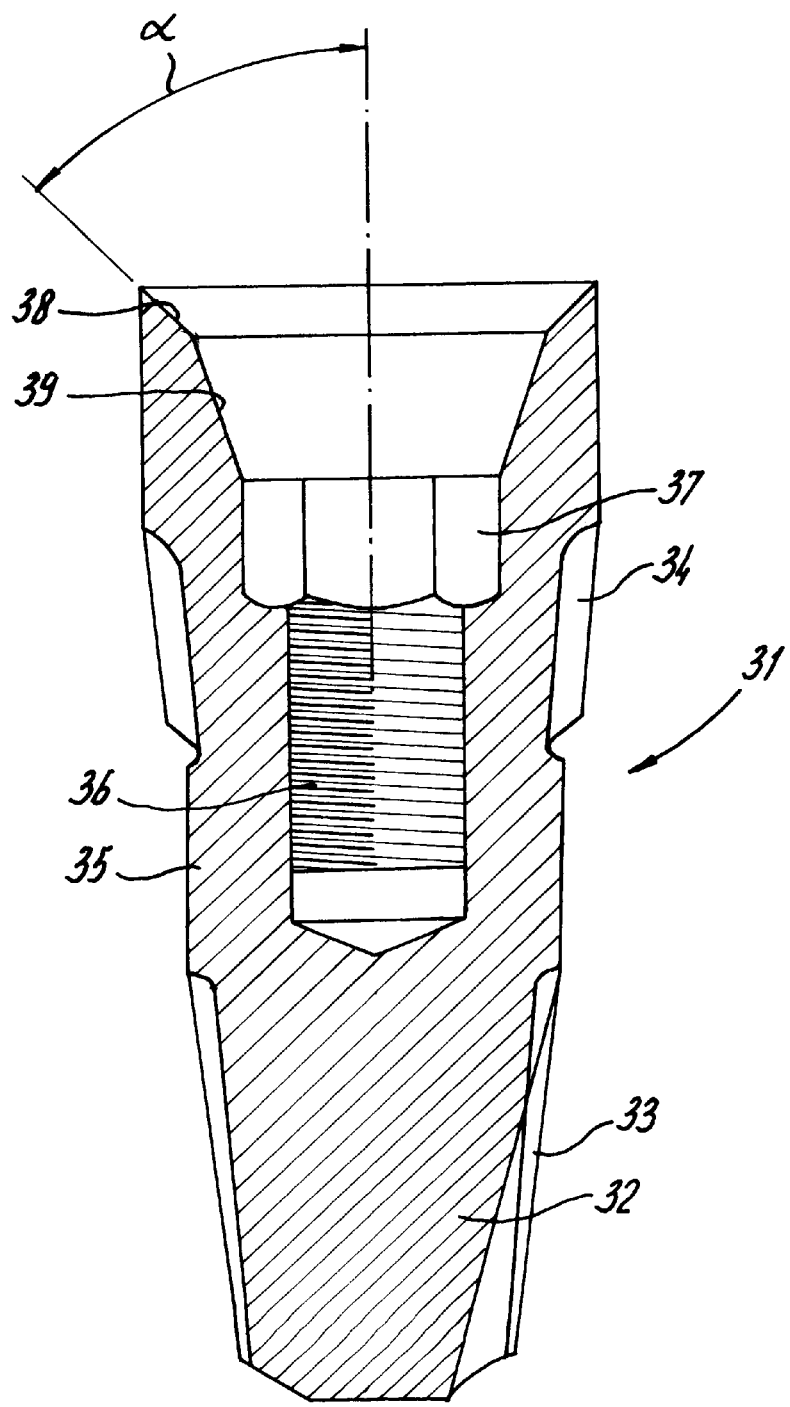
FIG. 5 shows, in cross-section corresponding to FIG. 1, a third embodiment of a dental implant according to the invention.

FIG. 5 shows a further embodiment of an implant according to the invention which can be used either in combination with a set of dental implants that has been described above or on its own. This implant is indicated in its entirety by 31. A shaft section 32 is present, provided with a conical threaded section 33. A further conical threaded section is indicated by 34, whilst 35 indicates a cylindrical section. Just as in the case of the previous embodiments, the length of said section 35 is dependent on a number of factors, such as the thickness of the patient's jawbone, and there are various lengths available to the dentist. The top section of the implant 31 differs in construction from what has been shown in the previous figures. There is a threaded section 36 in the interior of the cylindrical section 35. An internal hexagon 37 adjoins this. This internal hexagon 37 serves for fixing the subsequent secondary component such that it cannot be turned. A conical section, consisting of a first conical section 38 and a second conical section 39, adjoins said hexagon 37. Conical section 38 is designed to engage on an insertion instrument. That is to say, in contrast to the prior art, the instrument no longer engages on the internal hexagon 37 but on the conical section 38. The second conical section 39 can optionally be of cylindrical construction.

Figure 3:
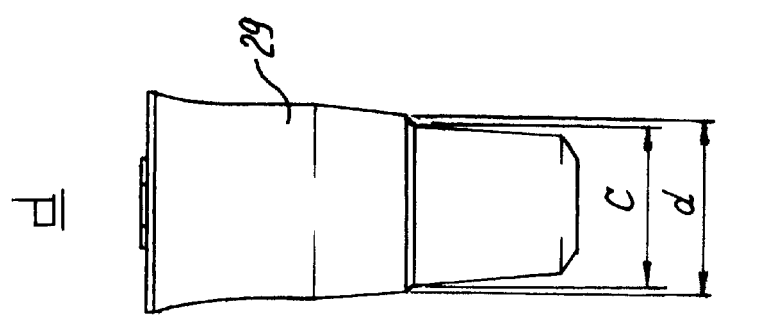
FIG. 3 shows a series of dental implants.
Figure 3:
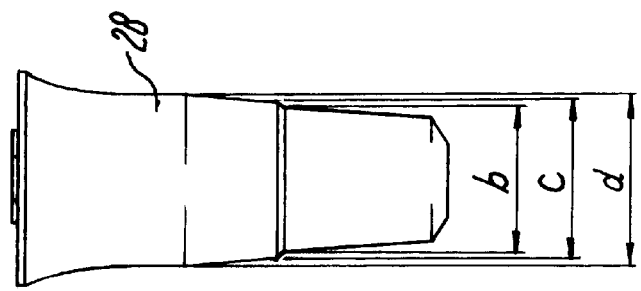
Figure 3:
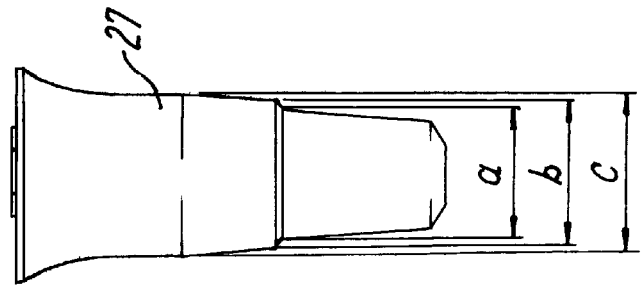
Figure 3:
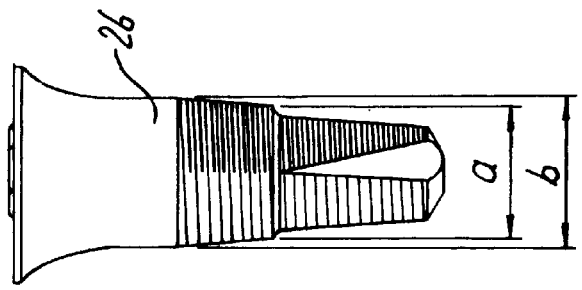
Figure 4:
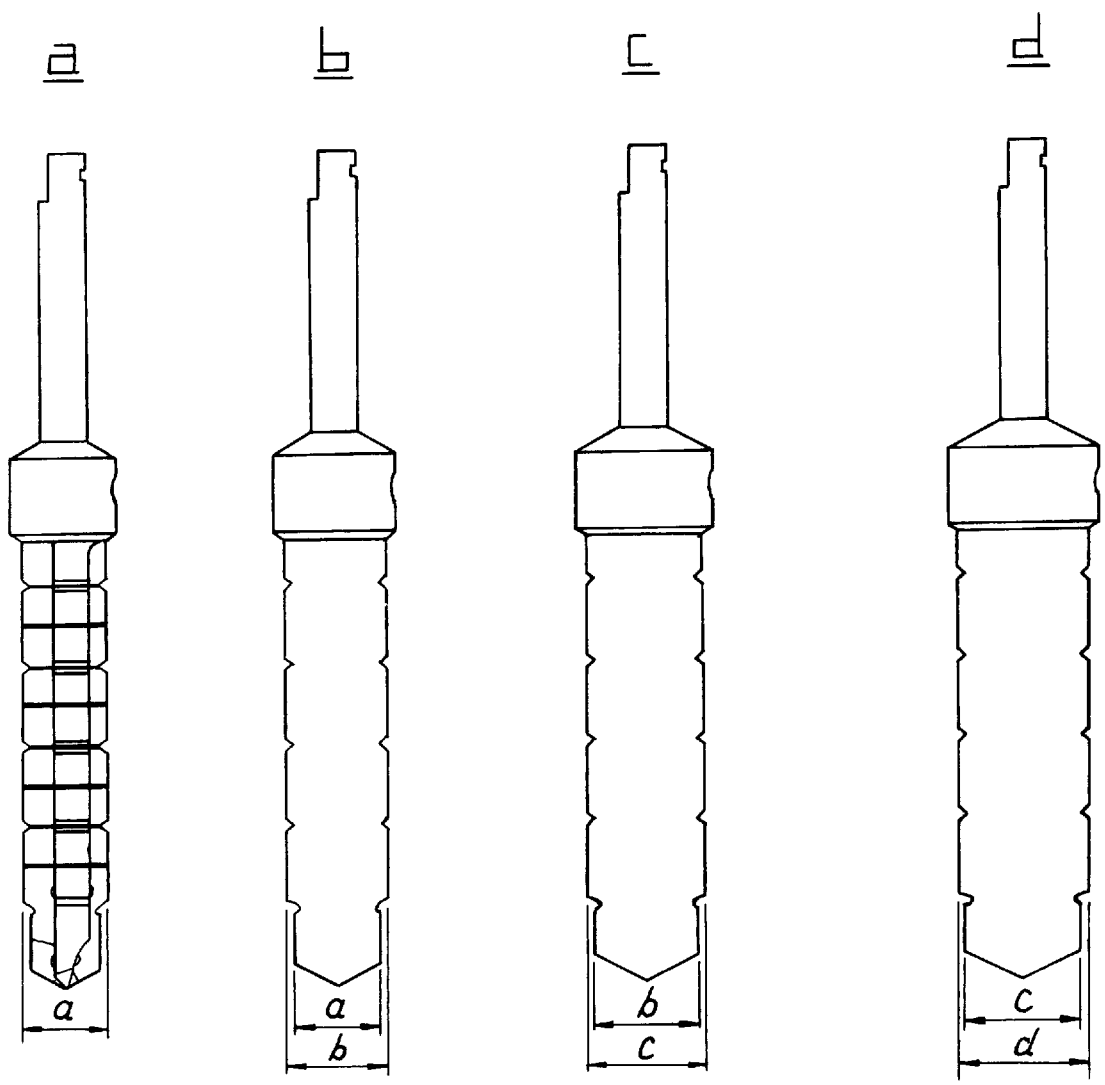
FIG. 4 shows a series of drills to be used with the implants according to FIG. 3.

A series of implants are shown in FIG. 3. These each have stepped sections. The various implants are indicated by the reference numerals 26–29, whilst the drill diameters of the stepped sections are indicated by 'a–c'. It is emphasised that it is drill diameters that are concerned here, that is to say that the final diameter of the implant can deviate as a result of deformation of the bone material, for example during cutting of screw thread.

It can be seen from FIG. 3 that implant 26 is smaller than implant 27. The drill diameter for the largest stepped section, or the head, is indicated by 'a' and this corresponds to the drill diameter a of the smallest stepped section, or base 'b', of implant 27. Consequently a restricted number of drills can suffice. In this context it is also important to distinguish between situations where the bone material of the jaw is relatively soft and where said bone material is relatively hard. In the case of a hard material it is necessary to cut screw thread and possibly to carry out an additional drilling operation before that time. The implants shown in FIG. 3 are not provided with a smooth section 5, as shown in FIG. 1. In principle, the aim when fitting implants is to have as much grip as possible on the jaw concerned. The marrow present between the hard outer shells of the jaw offers less support than said outer shells themselves. The aim, therefore, is so to adjust the length of the implant such that engagement on said hard material takes place both at the top and at the bottom. The length of the implant is measured depending on this. According to the invention this can take place in a particularly simple manner by adjusting the length of section 5.

The length of the top section of the implant, that is to say of the 'head', will not change as a result of adjustment of the length of section 5. Consequently, in the case of the drilling technique described above, the second drill can always be inserted into the jaw to the same depth. The first drill, that is to say the drill for the bottom screw thread, must, of course, be inserted into the jaw to the correct depth and this will be dependent on the length of the smooth section 5.

In the manner shown in FIG. 3, a simple composition of a series of implants having both different length and different diameter can be obtained and only a very limited number of drills shown in FIG. 4a–d is necessary in order to be able to fit such a series of implants. It will be understood that the diameter of the implant is dependent on the amount of bone material found and the size of the superstructure. Although such a series of implants is preferably constructed as shown in FIGS. 1 and 2, the end close to the superstructure to be fitted can also be implemented in accordance with any other construction known from the prior art.

Although the invention has been described above with reference to preferred embodiments, it must be understood that numerous modifications can be made thereto without going beyond the scope of the present invention as claims in the appended claims.

What is claimed is:

1. A set of dental implants comprising: a series of at least two implants, each implant having a different diameter, each implant being stepped and having a smaller section and a larger section, and the smaller section of an implant having a drill diameter which corresponds to the drill diameter for the larger section of a subsequent smaller implant.

2. The set according to claim 1, wherein at least one of said dental implants comprises a shaft having a first end structured and arranged to be provided with a superstructure and an opposite second insertion end, said shaft having proximate to the first end an external engagement surface for engaging an instrument adapted to screw in the implant, and for receiving said superstructure; said external engagement surface being at least partially surrounded by a peripheral collar located at a distance therefrom and extending from the shaft.

3. The set according to claim 2, wherein the internal boundary surface of the peripheral collar is conical at least proximate to a free end of the surface.

4. The set according to claim 3, wherein the conical collar makes a cone angle α ranging between 40 and 50° with respect to a longitudinal axis of the shaft.

5. The set according to claim 4, wherein the cone angle is about 45°.

6. The set according to claim 5, further comprising a self-tapping conical threaded section proximate to the insertion end, and a conical threaded section proximate to the first end.

7. The set according to claim 3, wherein at least one of the dental implants comprises from the insertion end a tapering first thread section, an adjoining cylindrical section, a tapering second thread section having a core diameter which at least corresponds to the core diameter of the first thread section, and an adjoining free end section; said cylindrical section comprising an internal threaded section having adjoining means for preventing rotation of a subsequent structure, and a conical end section structured and arranged to engage with a tool.

8. The set according to claim 7, wherein said at least one of the dental implants further comprises a conical section which adjoins said conical end section.

9. The set according to claim 3, wherein the shaft is a stepped shaft.

* * * * *